(12) United States Patent
Hill

(10) Patent No.: US 12,213,863 B2
(45) Date of Patent: Feb. 4, 2025

(54) THERAPEUTIC RECOVERY DEVICE FOR MEDICAL REHABILITATION

(71) Applicant: Franklin Robert Hill, Jacksonville, FL (US)

(72) Inventor: Franklin Robert Hill, Jacksonville, FL (US)

( * ) Notice: Subject to any disclaimer, the term of this patent is extended or adjusted under 35 U.S.C. 154(b) by 0 days.

(21) Appl. No.: 17/892,023

(22) Filed: Aug. 19, 2022

(65) Prior Publication Data

US 2024/0058178 A1 Feb. 22, 2024

(51) Int. Cl.
*A61F 13/14* (2006.01)
*A61F 7/02* (2006.01)

(52) U.S. Cl.
CPC .............. *A61F 13/143* (2013.01); *A61F 7/02* (2013.01); *A61F 2007/0219* (2013.01); *A61F 2007/0228* (2013.01)

(58) Field of Classification Search
CPC ...... A61F 5/00; A61F 5/02; A61F 5/03; A61F 5/3753; A61F 5/022; A61F 13/143; A61F 7/02; A61F 2007/0219; A61F 2007/0228; A61F 13/00; A61G 15/00; A41F 5/00; A41B 13/10; A41B 13/103; A41B 13/106; A41D 13/04; A41D 13/046; A41D 2300/33
USPC ........................................................ 602/75
See application file for complete search history.

(56) References Cited

U.S. PATENT DOCUMENTS

| | | | | |
|---|---|---|---|---|
| 5,692,246 A | * | 12/1997 | Benedick | A41D 13/1245 2/92 |
| 6,830,050 B1 | * | 12/2004 | Bamdad | A61F 5/3753 128/845 |
| 2017/0100300 A1 | * | 4/2017 | Rapp | A61B 5/6828 |
| 2018/0318120 A1 | * | 11/2018 | Oliver | A61F 7/10 |
| 2019/0100300 A1 | * | 4/2019 | Haldeman | B64C 27/48 |
| 2021/0138184 A1 | * | 5/2021 | Lois | A61M 21/02 |

* cited by examiner

*Primary Examiner* — Alireza Nia
*Assistant Examiner* — Daniel A Miller
(74) *Attorney, Agent, or Firm* — Wilson Dutra, PLLC; Camille A. Wilson

(57) ABSTRACT

The present disclosure provides generally for a therapeutic recovery device for medical rehabilitation. The therapeutic recovery device may comprise a compression device. The compression device may provide compressive force that provides relief. The therapeutic recovery device may comprise at least one securing mechanism. When the therapeutic recovery device comprises at least one sensor, the at least one sensor may provide feedback on the user's health. The therapeutic recovery device may comprise one or more straps. The one or more straps may allow the therapeutic recovery device to be secured in a plurality of orientations. The therapeutic recovery device may comprise at least one holder. When the therapeutic recovery device comprises at least one holder, the holder may comprise one or more pockets. The therapeutic recovery device may interface with at least one external device. The therapeutic recovery device may comprise a cover. When the therapeutic recovery device comprises a cover, the therapeutic recovery device may comprise at least one internal material that is removable insertable.

19 Claims, 5 Drawing Sheets

THERAPEUTIC RECOVERY DEVICE FOR MEDICAL REHABILITATION

BACKGROUND

Every year, hundreds of thousands of sternotomies are performed in the United States. A sternotomy is an incision used in cardiothoracic surgery to provide access directly to the thoracic cavity through the sternum. In other words, a sternotomy is a cut down the middle of the patient's chest to perform surgeries on the heart, lungs, and other areas in the chest. Sternotomies are most commonly used in open heart surgeries, and their usage in cardiothoracic surgeries is not likely to decrease, as cardiovascular and lung diseases continue to increase year by year. The other region of the torso, the abdomen, also sees its fair share of invasive surgeries such as appendectomies, colectomies, and other intestinal procedures. The recovery process following any invasive procedure done on the torso can be long and uncomfortable.

The recovery process following an open-heart surgery typically requires a patient to cough often and engage in deep breathing exercises. Because a sternotomy requires the sternum to be broken, an injury that takes several weeks to heal, actions such as deep breathing, coughing, and sneezing can prove to be quite painful for the patient. In addition to physical discomfort and pain, everyday actions can also cause complications in the healing process. To close a sternotomy, the sternum is wired shut, but with too much uncontrolled coughing and sneezing, the wires may loosen and compromise the healing process.

Medical professionals can prescribe medication to ease a patient's pain and discomfort while they recover from a sternotomy, but there is not much else they can do for the patient's physical ailments until they are able to begin their rehabilitation. To provide comfort to recovering sternotomy patients, they are often given rehabilitative pillows to reduce pain caused by coughing, breathing, and sneezing.

The act of embracing a rehabilitative pillow while coughing, breathing, or sneezing can dampen the forces associated with these events and reduce the amount of pain and discomfort felt by the patient. Aside from aiding the patient's comfort, the dampening effect created by the rehabilitative pillows is used as a way to counter the pressure caused by coughing and sneezing that could potentially cause damage to the surgical site.

A sternotomy takes a physical toll on a patient and requires an extended stay in a hospital. After a surgery, patients often find themselves fatigued and physically limited in their mobility, strength, and dexterity while they recover. Because of the physical toll that is left by the procedure; patients often find themselves too fatigued to constantly hold a rehabilitative pillow against their chest or to continue to be reaching for it every time they need to cough or sneeze.

When a rehabilitative pillow gets dropped or otherwise moved to an out-of-reach location, the patient must then exert themselves rather abruptly to suppress their coughs or sneezes. Although patients benefit from the physical and emotional effects of the rehabilitative pillow, by having to exert extra effort for every cough or sneeze, the effects may prove to be more detrimental than beneficial.

SUMMARY OF THE DISCLOSURE

What is needed is a therapeutic recovery device that can provide post-surgical relief without requiring high levels of exertion from a patient. A therapeutic recovery device that can supply consistent compression without requiring the patient to exert consistent levels of pressure on the therapeutic recovery device is also desired.

The present disclosure provides generally for a therapeutic recovery device for medical rehabilitation. The therapeutic recovery device may comprise a compression device. The compression device may provide compressive force that provides relief. The therapeutic recovery device may comprise at least one securing mechanism.

In some aspects wherein at least a portion of the therapeutic recovery device, such as the compression device, may comprise at least one sensor, the at least one sensor may provide feedback on a user's health. The therapeutic recovery device may comprise one or more straps. The one or more straps may allow the therapeutic recovery device to be secured in one of a plurality of potential orientations.

The therapeutic recovery device may comprise at least one holder. When the therapeutic recovery device comprises a holder, the holder, or any other portion of the therapeutic recovery device, may comprise one or more pockets. The therapeutic recovery device may interface with at least one external device. The therapeutic recovery device may comprise a cover. The therapeutic recovery device may comprise at least one internal material. When the therapeutic recovery device comprises a cover, the therapeutic recovery device may comprise at least one internal material that may be removably insertable

BRIEF DESCRIPTION OF THE DRAWINGS

The accompanying drawings that are incorporated in and constitute a part of this specification illustrate several embodiments of the disclosure and, together with the description, serve to explain the principles of the disclosure.

DETAILED DESCRIPTION

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Holder: As used herein, refers to an amount of material attached to an interior side of a compression device of a therapeutic recovery device with at least one opening for the purpose of at least partially receiving and resting therein an arm, hand, or any other limb or appendage of a user, or one or more portions thereof, in the holder while retaining compressive force against the body of the user via the compression device. In some embodiments, the holder may comprise both horizontally-oriented and vertically-oriented openings to provide utility regardless of the orientation of the therapeutic recovery device.

Figure 1A:
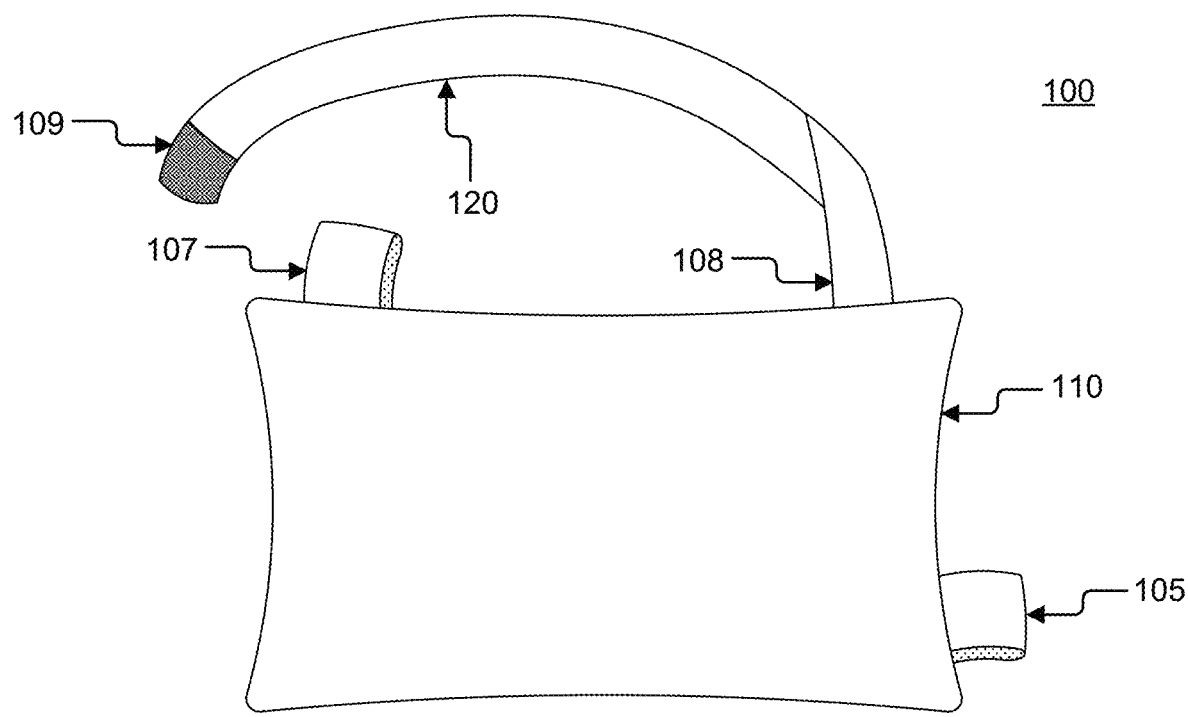
FIG. 1A illustrates a front view of an exemplary therapeutic recovery device, according to some embodiments of the present disclosure.
Figure 1B:
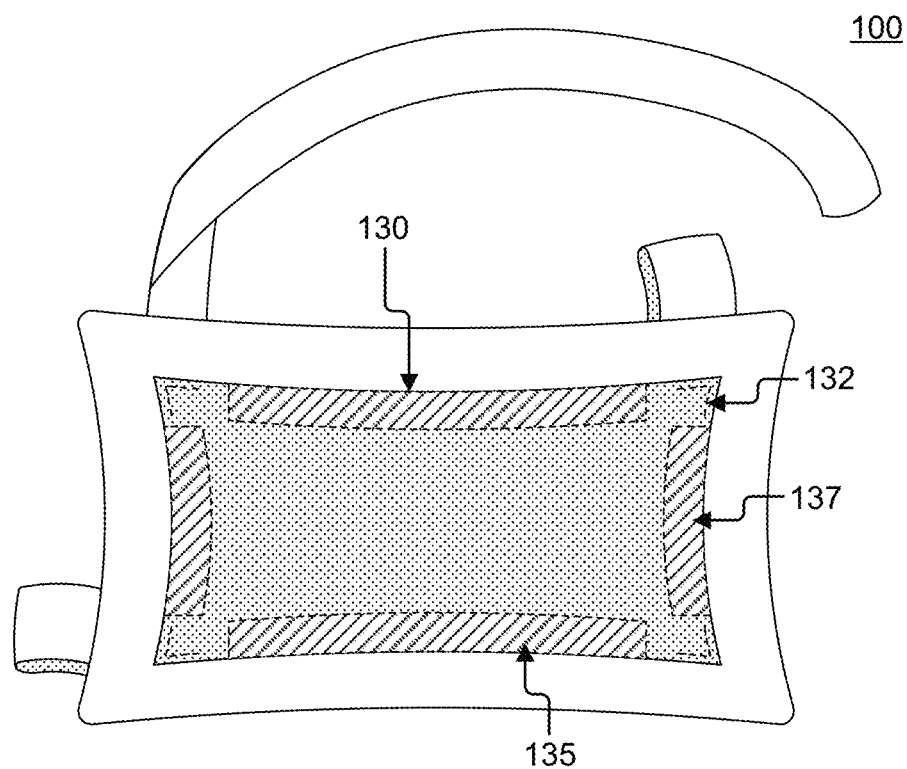
FIG. 1B illustrates a rear view of an exemplary therapeutic recovery device, according to some embodiments of the present disclosure.
Figure 1C:
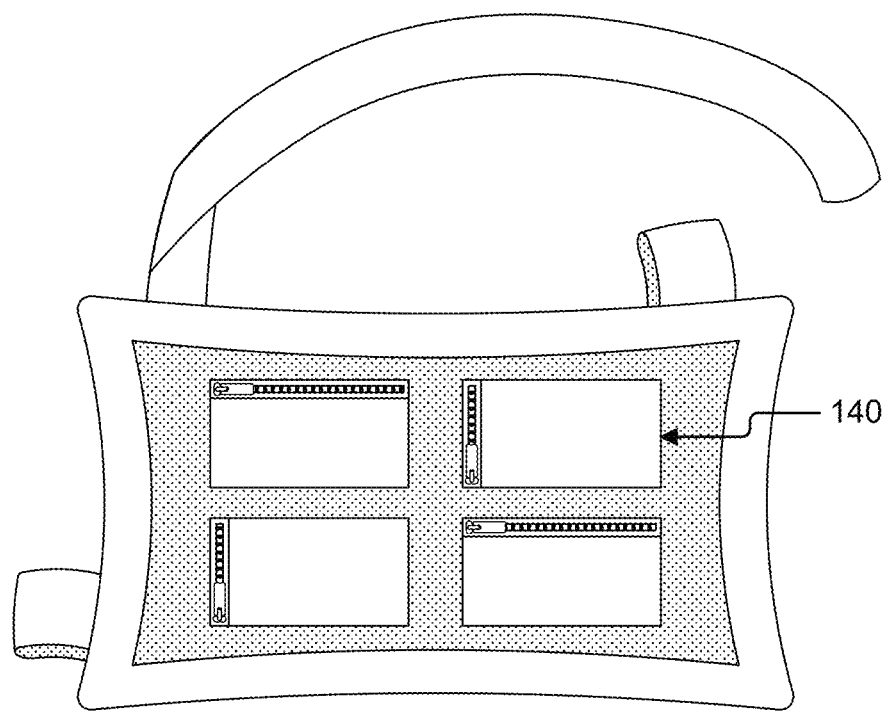
FIG. 1C illustrates a rear view of an exemplary therapeutic recovery device, according to some embodiments of the present disclosure.

Referring now to FIGS. 1A-C, front and rear views of an exemplary therapeutic recovery device 100 are illustrated. In some embodiments, the therapeutic recovery device 100 may comprise one or more straps 120. In some implementations, the therapeutic recovery device 100 may comprise a plurality of straps 120. In some aspects, the therapeutic recovery device 100 may comprise a compression device 110 configured to be pressed against at least a portion of the body of a user to exert a compressive force against the at least a portion of the body of the user, such as, by way of example and not limitation, the user's torso.

In some embodiments, the therapeutic recovery device 100 may comprise at least one holder 130. In some implementations, the therapeutic recovery device 100 may comprise at least one pocket 140. In some aspects, the therapeutic recovery device 100 may comprise a plurality of pockets 140.

In some embodiments, one or more straps 120 may allow the compression device 110 to be secured in one of a plurality of potential positions or orientations. For example, a first end 108 of an extended strap 120 may be secured to and protrude from one corner of the compression device 110 with the option to removably attach the second end 109 of the strap 120 to either of two separate securing mechanisms 105, 107 on both adjacent corners of the compression device 110.

By connecting to the first securing mechanism 105, the compression device 110 may hang from the strap 120 in a vertical orientation. By detaching from the first securing mechanism 105 and attaching to the second securing mechanism 107, the compression device 110 may hang from the strap 120 in a horizontal orientation.

In some implementations, at least one of the straps 120 may extend around and embrace at least a portion of a user's body, such as the torso, to maintain the compression device 110 in a desired location or position. In some aspects, the holder 130 may assist in securing the therapeutic recovery device 100 in place in addition to or instead of strap(s) 120.

In some aspects, the holder 130 may provide a location to place at least a portion of a limb or appendage, such as a user's arm and/or hand, to keep the compression device 110 close to the body of the user. The increased proximity of the compression device 110 may assist in providing compression from the compression device 110 that reduces pain and discomfort that may be experienced after surgery. In some embodiments, the holder 130 may allow the user to passively retain the compression device 110 against the user's body while allowing one hand to remain free for purposes other than engaging the compression device 110.

In some implementations, the holder 130 may comprise at least one opening 135, 137. In some embodiments, the holder 130 may comprise at least one vertically-oriented opening 137 and at least one horizontally-oriented opening 135. In some aspects, a plurality of vertical and horizontal openings 137, 135 may allow the therapeutic recovery device 100 to be retained in any one of a plurality of potential orientations.

For example, the vertical openings 137 may allow the holder 130 to secure an arm while the compression device 110 is in a vertical orientation. If the compression device 110 is switched to a horizontal orientation, then the horizontal openings 135 may allow the holder 130 to secure an arm while the compression device 110 is in the horizontal orientation.

In some embodiments, the holder 130 may comprise a method of securing or closing, or both, any unused openings. As an illustrative example, the holder 130 may comprise at least one fastening element, such as, by way of example and not limitation, a hook-and-loop fastener, snap-fit element, zipper, clamp, clasp, clip, snap, pin, hole, or any similar mechanism, as well as any combination thereof, to close or secure any unused openings.

In some implementations, the therapeutic recovery device 100 may comprise one or more pockets 140. In some embodiments, the pockets 140 may be attached to or integrated with the compression device 110, such as, for example and not limitation, by being attached to an exterior surface of the compression device 110.

In some implementations, the pockets 140 may be connected to or integrated with the holder 130. In some aspects, the pockets 140 may comprise at least one fastening element. In some embodiments, a plurality of pockets 140 may comprise a combination of vertical and horizontal orientations.

The combination of vertical and horizontal orientations may provide accessible pockets 140 to a user regardless of the orientation of the compression device 110. In some implementations, one or more fastening elements may retain items within pockets 140 that are oriented in a position perpendicular to their constructed orientation upon the compression device 110.

For example, a vertically-oriented pocket 140 upon the compression device 110 may, because of a fastening element in the form of a zipper, retain items within the pocket 140 even when the compression device 110 is placed in a horizontal orientation.

In some aspects, the compression device 110 may comprise an exterior surface, wherein the exterior surface faces away from the body of the user during use. In some implementations, the compression device 110 may comprise an interior surface, wherein the interior surface is on the opposite surface of the compression device 110 from the exterior surface and faces towards the body of the user during use.

In some embodiments, the compression device 110 may comprise a first distal end where a first edge of the exterior surface and a first edge of the interior surface converge. In some implementations, the compression device 110 may comprise a second distal end where a second edge of the exterior surface and a second edge of the interior surface converge, and wherein the second distal end is opposite to the first distal end.

In some aspects, the compression device 110 or one or more other portions of the therapeutic recovery device 100 may comprise at least one internal material, such as, by way of example and not limitation, cotton, foam, polyester, or any similar at least partially pliable materials, as well as any combination thereof. In some implementations, by comprising one or more at least partially pliable internal materials, the compression device 110 may comprise a padded configuration, which may facilitate user comfort when the compression device 110 is placed against a torso or other region of the user's body.

In some embodiments, the at least one internal material may at least partially comprise a weighted material or one or more weighted elements. In some embodiments, the at least one internal material may be removably insertable into at least a portion of the therapeutic recovery device 100, such as, by way of example and not limitation, the compression device 110.

In some aspects, the compression device 110 may comprise two substantially straight side portions on opposing sides of the compression device 110, the two substantially straight side portions extending from the first distal end to the second distal end.

In some embodiments, the compression device 110 may comprise at least one holder 130, wherein the at least one holder 130 comprises a retaining portion and is attached to or integrated with the interior surface of the compression device, wherein the at least one holder 130 is configured to at least partially receive at least a portion of at least one of a user's limbs and/or appendages, such as at least a portion of one of the user's hands and/or arms. In some implementations, the holder 130 may be secured to the interior surface of the compression device 110 at one or more attachment locations 132, such as, for example and not limitation, via stitching or adhesion. In some aspects, the holder 130 may comprise at least one opening 135, 137 between every adjacent attachment location 132. In some non-limiting exemplary embodiments, the holder 130 may comprise four attachment locations 132, wherein each attachment location 132 may be configured at or proximate to a corner of the holder 130.

In some implementations, each of the one or more straps 120 may comprise a first end 108 and a second end 109. In some embodiments, the second end 109 of each strap 120 may be removably attachable to the compression device 110 via at least one securing mechanism 105, 107. By way of example and not limitation, the securing mechanism 105, 107 may comprise a loop of material or fabric, a clamp, a clasp, a clip, at least one hook-and-loop fastener, a hook, a hole, a buckle, or any similar element or mechanism, as well as any combination thereof.

In some aspects, one or both of the first end 108 and the second end 109 of each strap 120 and/or one or more securing mechanisms 105 may remain securely attached to the compression device 110 in a non-removable fashion, such as, by way of example and not limitation, by being sown to, stitched to, adhered to (such as via one or more adhesives), or integrated with the compression device 110.

The first and/or second end 108, 109 of each strap 120 or securing mechanism 105 may extend from or be securely attached to any appropriate portion of the therapeutic recovery device 100, including but not limited to the first distal end, the second distal end, one or both of the substantially straight side portions, or at least one corner of the compression device 110.

In some implementations, the at least one securing mechanism 105 may be configured to adjust a length of a usable portion of each strap 120, thereby adjusting how tightly the compression device 110 is pressed against the body of a user and simultaneously adjusting the amount of compressive force the compression device 110 exerts upon the user's body.

For example, in aspects wherein the securing mechanism 105 may comprise a buckle, the buckle may be alterable between an open state and a secured state, wherein a portion of at least one strap 120 may be slidable through the buckle when the buckle is in the open state, thereby allowing the length of the usable portion of the strap 120 to be adjusted. By way of example and not limitation, a usable portion of a strap 120 may comprise a portion of the strap 120 that is available to encircle, enclose, or embrace at least a portion of a user's body.

Figure 2A:
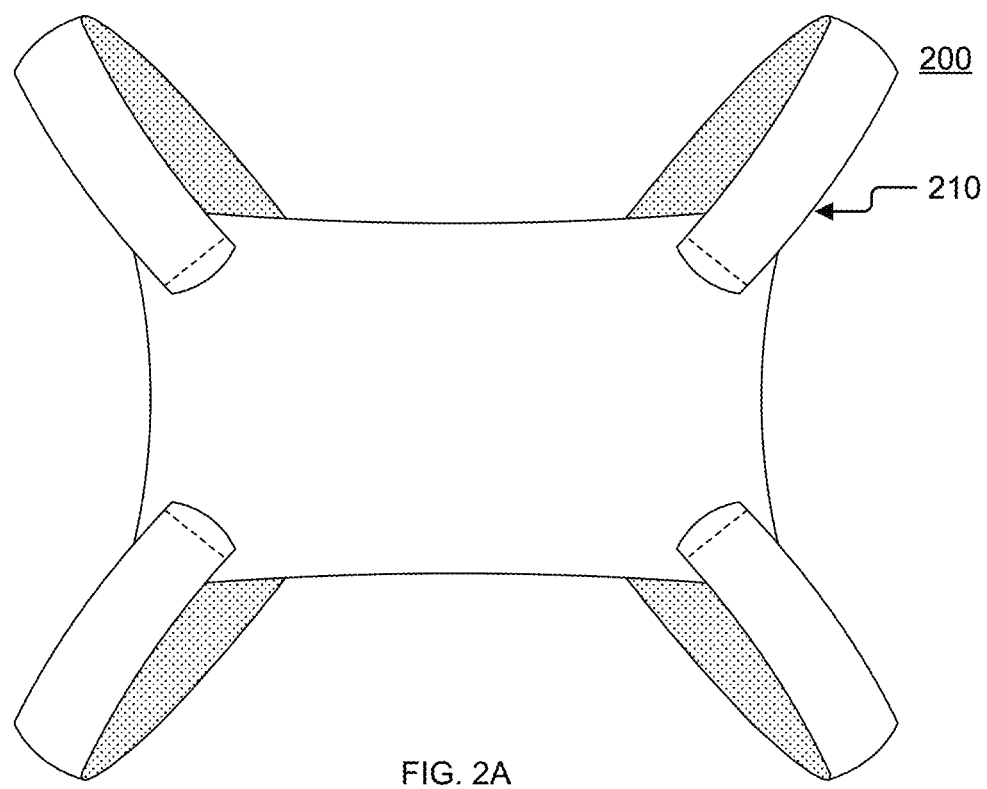
FIG. 2A illustrates a front view of an exemplary therapeutic recovery device comprising straps, according to some embodiments of the present disclosure.
Figure 2B:
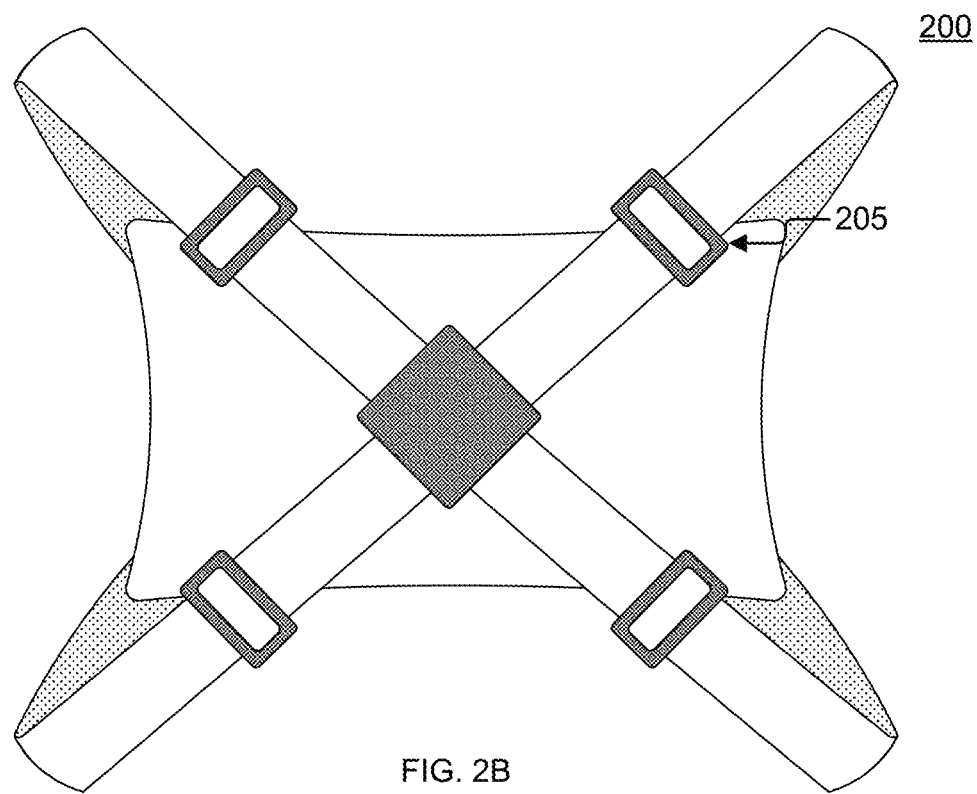
FIG. 2B illustrates a rear view of an exemplary therapeutic recovery device comprising straps, according to some embodiments of the present disclosure.

Referring now to FIGS. 2A-B, front and rear views of an exemplary therapeutic recovery device 200 comprising straps 220 are illustrated. In some embodiments, the therapeutic recovery device 200 may comprise a plurality of straps 220. In some implementations, the therapeutic recovery device 200 may comprise a compression device 210.

In some aspects, the therapeutic recovery device 200 may comprise at least one securing mechanism 205. In some embodiments, at least one of the plurality of straps 220 may be adjustable. In some implementations, at least one of the plurality of straps 220 may be adjustable via the securing mechanism 205.

As an illustrative example, at least one of the straps 220 may comprise a tightening buckle that allows a user to tighten one or more loops of strap 220 fixed to the compression device 210 to increase the proximity of the compression device 210 to the user when worn. Securing the therapeutic recovery device 200 via adjustable straps 220 may allow the therapeutic recovery device 200 to be held in a compressive state against the body of the user without the use of the user's hands. This may allow the user to use their hands for other purposes rather than be occupied by engaging the compression device 210.

Figure 3A:
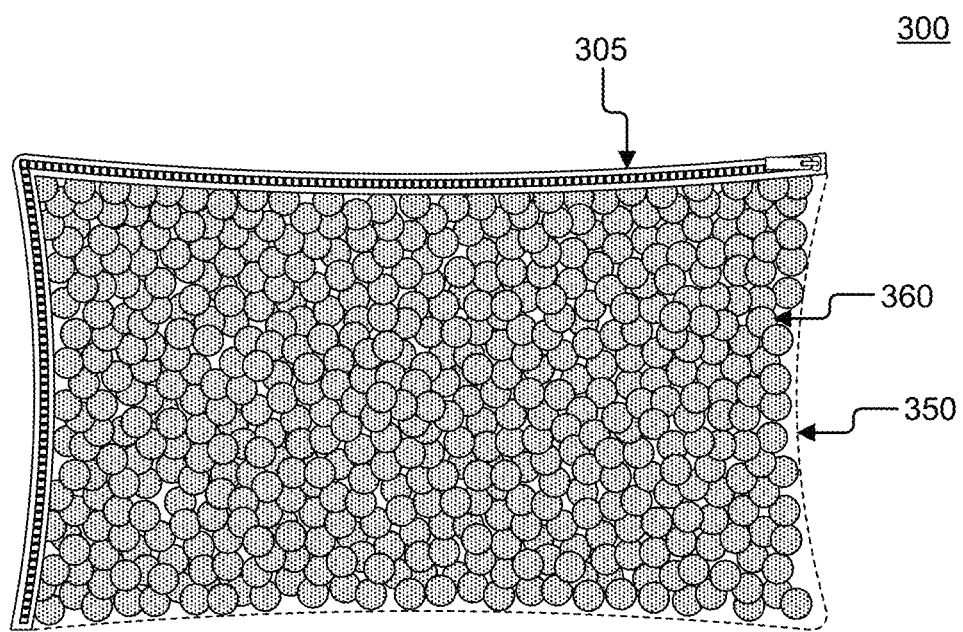
FIG. 3A illustrates a front view of an exemplary therapeutic recovery device comprising an insertable material, according to some embodiments of the present disclosure.
Figure 3B:
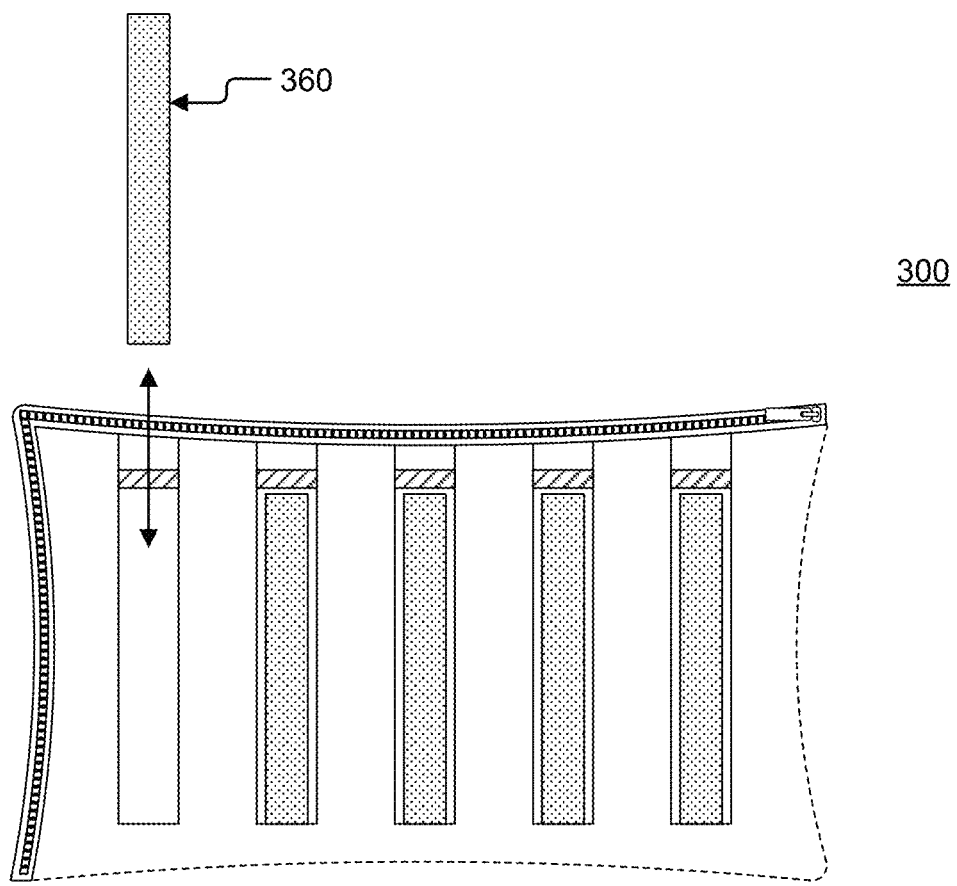
FIG. 3B illustrates a front view of an exemplary therapeutic recovery device comprising an insertable material, according to some embodiments of the present disclosure.

Referring now to FIGS. 3A-B, front views of an exemplary therapeutic recovery device 300 comprising an insertable material 360 are illustrated. In some embodiments, the therapeutic recovery device 300 may comprise a compression device 310. In some implementations, the therapeutic recovery device 300 may comprise a cover 350. In some aspects, the therapeutic recovery device 300 may comprise at least one internal removably insertable material 360. In some embodiments, the therapeutic recovery device 300 may comprise at least one securing mechanism 305.

In some implementations, the cover 350 may comprise the insertable material 360. In some aspects, the cover 350 may be removable. In some embodiments, the cover 350 may attach to the therapeutic recovery device 300 via at least one securing mechanism 305, such as a zipper, as a non-limiting example.

In some implementations, the insertable material 360 may be inserted directly into at least one portion of the compression device 310. In some aspects, the insertable material 360 may be inserted into preconfigured slots within the compression device 310 that are created to receive the insertable material 360.

In some embodiments, the insertable material 360 or other internal material may improve the comfort provided by the therapeutic recovery device 300. For example, an insertable material 360 that at least partially comprises a weighted material or one or more weighted elements may provide comfort similar to a weighted blanket.

As another example, the insertable material 360 may comprise a material or object that may retain a fixed temperature or that may change temperature, such as, by way of example and not limitation, one or more heating elements (such as, for example, one or more hot or heat packs at least partially comprising an amount of magnesium sulfate or calcium chloride), an amount of cooling fabric or cooling gel (such as, for example, sodium polyacrylate), as well as any similar elements or any combination thereof.

Controlling the temperature of the therapeutic recovery device 300 may make wearing the therapeutic recovery device 300 more comfortable or may aid with recovery by applying temperatures conducive for reducing swelling, as non-limiting examples.

Figure 4A:
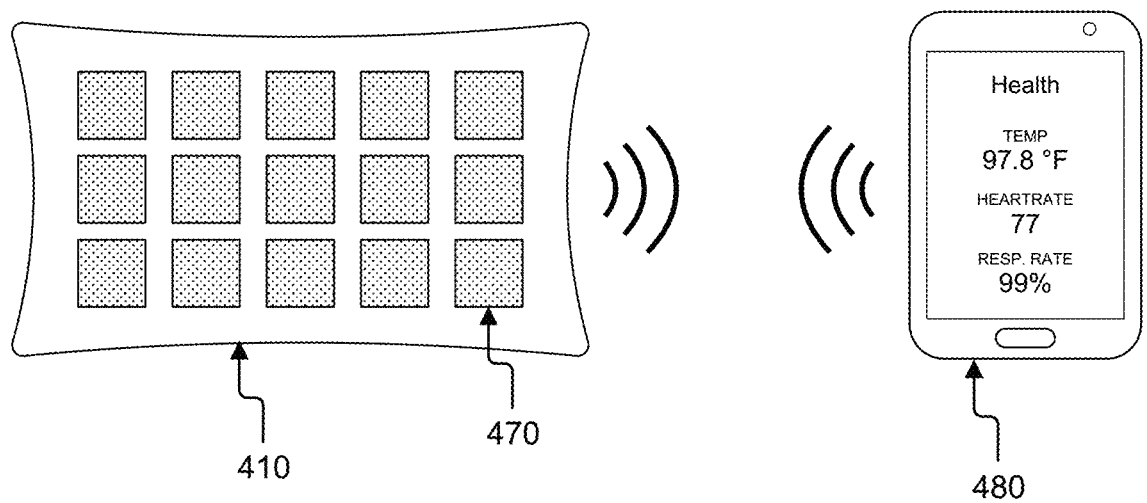
FIG. 4A illustrates a front view of an exemplary therapeutic recovery device interfacing with an external device, according to some embodiments of the present disclosure.
Figure 4B:
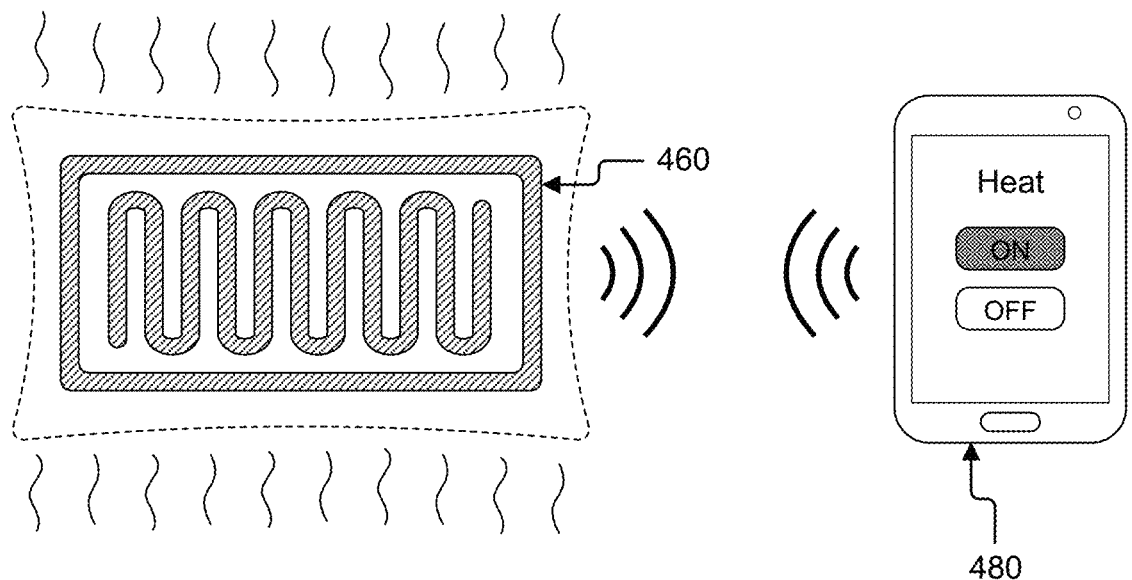
FIG. 4B illustrates a front view of an exemplary therapeutic recovery device interfacing with an external device, according to some embodiments of the present disclosure.

Referring now to FIGS. 4A-B, front views of an exemplary therapeutic recovery device 400 interfacing with an external device 480 are illustrated. In some embodiments, at least a portion of the therapeutic recovery device 400, such as, by way of example and not limitation, a compression device 410, may comprise at least one sensor 470. In some aspects, the at least one sensor 470 may be attached to or integrated with an outer portion or cover of the therapeutic recovery device 400.

In some implementations, the therapeutic recovery device 400 may comprise a plurality of sensors 470. In some embodiments, the therapeutic recovery device 400 may be configured to interface with at least one external device 480. In some implementations, the therapeutic recovery device 400 may comprise at least one internal removably insertable material 460. In some aspects, the at least one sensor 470 may comprise at least one of: a pulse oximeter, a thermometer, a heart rate monitor, an accelerometer, a pressure sensor, and a motion sensor, as well as any similar device.

In some embodiments, at least one of the sensors 470 may be configured to provide or transmit biofeedback data or other information associated with a user to the external device 480, such as oxygen (O2) levels, body temperature, heart rate, and restlessness during sleeping, as a list of non-limiting examples.

For example, at least one of the sensors 470 may measure a heart rate when the compression device 410 is in close contact with the user. As another example, the sensors 470 may comprise at least one sensor 470 that detects oxygen levels of the user while the therapeutic recovery device 400 is close to the user while sleeping. By way of example and not limitation, the user's oxygen levels may be detected by at least one sensor 470 in the form of a pulse oximeter or any similar oxygen detection or measurement device.

In some implementations, the external device 480 may be configured to communicate with the therapeutic recovery device 400 in a manner sufficient to alter or adjust a state (such as, for example and not limitation, a temperature) of the insertable material 460 or other internal material.

As an example, the insertable material 460 may comprise one or more heating or cooling elements, such as, by way of example and not limitation, one or more heating coils, that may be activated and controlled via a software application on a cellular phone, smartphone, tablet, or similar portable or desktop computing device communicatively coupled to a controller connected to or associated with the insertable material 460 or other internal material.

In some embodiments, the controller and/or one or more wires or other circuitry elements that may be associated therewith may be at least partially configured within a housing. In some aspects, the therapeutic recovery device 400 may comprise at least one power supply, such as, by way of example and not limitation, at least one battery; at least one solar cell or other photovoltaic element; at least one cord, cable, or wire configured to receive an amount of alternating current or direct current electricity, or any similar power supply or source, as well as any combination thereof.

In some implementations, the at least one power supply and any circuitry elements that may be associated therewith may be at least partially configured within the controller housing or within a separate independent housing. The at least one power supply may be configured to power one or more electrical or electromechanical components of the therapeutic recovery device 400, including but not limited to any sensors 470, heating or cooling elements, controllers, or circuitry elements that may be configured or associated with the therapeutic recovery device 400.

In some aspects, one or more sensors 470 may be configured to prompt activation of the internal insertable material 460 or other internal material. In such aspects, the relevant sensor(s) 470 may be communicatively coupled, either directly or indirectly, either wired or wirelessly, to the controller associated with the insertable material 460.

In some embodiments, activation of the insertable material 460 or other internal material may be at least partially based on a predetermined threshold value set by and received from the external device 480.

Continuing the previous example, the therapeutic recovery device 400 may comprise at least one sensor 470 in the form of a thermometer or other temperature sensor that, based on a predetermined temperature set within the application on the computing device, may be configured to activate the heating coils of the internal insertable material 460 to adjust the temperature of the therapeutic recovery device 400 when the temperature sensor detects that the temperature of the therapeutic recovery device 400 has decreased below the predetermined temperature.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A therapeutic recovery device comprising:
a compression device, wherein the compression device is configured to be pressed against at least a portion of a body of a user to exert a compressive force against the at least a portion of the body of the user, the compression device comprising:
an exterior surface, wherein the exterior surface faces away from the body of the user during use;
an interior surface, wherein the interior surface is on the opposite surface of the compression device from the exterior surface and faces towards the body of the user during use;
a first distal end, wherein a first edge of the exterior surface and a first edge of the interior surface converge at the first distal end;
a second distal end, wherein a second edge of the exterior surface and a second edge of the interior surface converge at the second distal end and the second distal end is opposite to the first distal end;
two straight side portions on opposing sides of the compression device, the two straight side portions extending from the first distal end to the second distal end; and
at least one holder, wherein the at least one holder comprises a retaining portion and is attached to the interior surface at three or more attachment locations, wherein the at least one holder is configured to receive at least one of: at least one limb of the user and at least one appendage of the user, wherein the at least one holder comprises at least one opening configured between adjacent attachment locations;
one or more straps, wherein each of the one or more straps comprises a first end and a second end, wherein the first end is secured to the compression device and the second end is attachable to a first securing mechanism or a second securing mechanism, and wherein the attaching of the second end to the first securing mechanism provides a horizontal orientation of the compression device and the attaching of the second end to the second securing mechanism provides a vertical orientation of the compression device.

2. The therapeutic recovery device of claim 1, wherein the compression device comprises at least one sensor.

3. The therapeutic recovery device of claim 2, wherein the compression device is configured to interface with at least one external device.

4. The therapeutic recovery device of claim 3, wherein the at least one sensor is configured to transmit data to the at least one external device.

5. The therapeutic recovery device of claim 4, wherein the compression device further comprises at least one internal material, wherein the at least one sensor is configured to activate the at least one internal material based on a predetermined value received from the at least one external device.

6. The therapeutic recovery device of claim 2, wherein the at least one sensor comprises at least one of: a pulse oximeter, a thermometer, a heart rate monitor, an accelerometer, pressure sensor, and a motion sensor.

7. The therapeutic recovery device of claim 1, wherein one or both the first securing mechanism and the second securing mechanism comprise one or more of: a loop, a clamp, a clasp, a clip, a hook-and-loop fastener, a hook, a hole, or a buckle.

8. The therapeutic recovery device of claim 7, wherein the first securing mechanism extends outwardly proximate to a first corner of the compression device and the second securing mechanism extends outwardly proximate to a second corner of the compression device.

9. The therapeutic recovery device of claim 8, wherein the first end of the one or more straps is secured proximate to a third corner of the compression device and the second end of the one or more straps is removably attachable to the compression device via at least one of the first securing mechanism or second securing mechanism, wherein the first and second corners of the compression device are adjacent to the third corner of the compression device.

10. The therapeutic recovery device of claim 7, wherein the first end and the second end of the one or more straps is securely attached to at least one of: the first distal end, the second distal end, at least one corner of the compression device, and at least one of the two straight side portions.

11. The therapeutic recovery device of claim 1, wherein the compression device further comprises at least one internal material, wherein the at least one internal material is at least partially pliable such that the compression device comprises a padded configuration.

12. The therapeutic recovery device of claim 11, wherein the at least one internal material is configured to adjust a temperature of the compression device.

13. The therapeutic recovery device of claim 12, wherein the at least one internal material comprises at least one of: one or more heating elements, an amount of cooling fabric, and an amount of cooling gel.

14. The therapeutic recovery device of claim 1, wherein the compression device further comprises a cover.

15. The therapeutic recovery device of claim 14, wherein the at least one internal material is removably insertable.

16. The therapeutic recovery device of claim 1, wherein the at least one holder comprises at least one vertically-oriented opening and at least one horizontally-oriented opening.

17. The therapeutic recovery device of claim 16, wherein the three or more attachment locations of the at least one holder is four attachment locations, wherein each attachment location comprises a corner of the at least one holder.

18. The therapeutic recovery device of claim 1, wherein the compression device further comprises one or more pockets, wherein the one or more pockets are attached to the exterior surface.

19. The therapeutic recovery device of claim 1, wherein the first securing mechanism and the second securing mechanism are configured to adjust a length of a usable portion of at least one of the one or more straps.

* * * * *